(12) United States Patent
Avraham et al.

(10) Patent No.: US 11,890,467 B2
(45) Date of Patent: Feb. 6, 2024

(54) DELIVERING TUMOR TREATING FIELDS (TTFIELDS) TO THE NECK

(71) Applicant: Novocure GmbH, Root (CH)

(72) Inventors: Yissachar Avraham, Haifa (IL); Ariel Naveh, Haifa (IL); Zeev Bomzon, Kiryat Tivon (IL)

(73) Assignee: Novocure GmbH, Root (CH)

( * ) Notice: Subject to any disclaimer, the term of this patent is extended or adjusted under 35 U.S.C. 154(b) by 344 days.

(21) Appl. No.: 17/005,622

(22) Filed: Aug. 28, 2020

(65) Prior Publication Data

US 2021/0060334 A1 Mar. 4, 2021

Related U.S. Application Data

(60) Provisional application No. 62/893,876, filed on Aug. 30, 2019.

(51) Int. Cl.
| | |
|---|---|
| *A61N 1/00* | (2006.01) |
| *A61N 1/36* | (2006.01) |
| *G16H 20/30* | (2018.01) |
| *G16H 50/50* | (2018.01) |
| *G06F 30/10* | (2020.01) |
| *A61N 1/04* | (2006.01) |
| *G01R 29/08* | (2006.01) |

(52) U.S. Cl.
CPC ....... *A61N 1/36002* (2017.08); *A61N 1/0408* (2013.01); *A61N 1/36034* (2017.08); *G01R 29/0807* (2013.01); *G06F 30/10* (2020.01); *G16H 20/30* (2018.01); *G16H 50/50* (2018.01)

(58) Field of Classification Search
None
See application file for complete search history.

(56) References Cited

U.S. PATENT DOCUMENTS

| | | |
|---|---|---|
| 6,868,289 B2 | 3/2005 | Palti |
| 7,016,725 B2 | 3/2006 | Palti |

(Continued)

FOREIGN PATENT DOCUMENTS

| | | |
|---|---|---|
| JP | 2002291910 A | 10/2002 |
| WO | 2004030760 A2 | 4/2004 |

OTHER PUBLICATIONS

International Search Report and Written Opinion issued in application No. PCT/IB2020/058047 dated Nov. 17, 2020.

*Primary Examiner* — John R Downey
*Assistant Examiner* — Anant A Gupta
(74) *Attorney, Agent, or Firm* — Potomac Law Group, PLLC (57) ABSTRACT

Tumor Treating Fields (TTFields) can be used to treat tumors (and/or prevent metastases) in or near a person's neck by affixing a first transducer array (i.e., a set of electrode elements) to the person's head and affixing a second transducer array to the person's chest. Subsequently, an AC voltage at a desired frequency (e.g., 100-300 kHz) is applied between the first transducer array and the second transducer array. This induces an electric field that is strong enough to be effective (e.g., greater than 1 V/cm) in most of the person's neck. In some embodiments, the center of the first transducer array is positioned on the vertex of the head or on an upper surface of the person's head. In some embodiments, the second set of electrode elements is positioned immediately below the base of the neck.

21 Claims, 8 Drawing Sheets

(56) References Cited

U.S. PATENT DOCUMENTS

| | | |
|---|---|---|
| 7,089,054 B2 | 8/2006 | Palti |
| 7,136,699 B2 | 11/2006 | Palti |
| 7,333,852 B2 | 2/2008 | Palti |
| 7,467,011 B2 | 12/2008 | Palti |
| 7,519,420 B2 | 4/2009 | Palti |
| 7,565,205 B2 | 7/2009 | Palti |
| 7,565,206 B2 | 7/2009 | Palti |
| 7,599,745 B2 | 10/2009 | Palti |
| 7,599,746 B2 | 10/2009 | Palti |
| 7,706,890 B2 | 4/2010 | Palti |
| 7,715,921 B2 | 5/2010 | Palti |
| 7,805,201 B2 | 9/2010 | Palti |
| 7,890,183 B2 | 2/2011 | Palti et al. |
| 7,912,540 B2 | 3/2011 | Palti |
| 7,917,227 B2 | 3/2011 | Palti |
| 8,019,414 B2 | 9/2011 | Palti |
| 8,027,738 B2 | 9/2011 | Palti |
| 8,170,684 B2 | 5/2012 | Palti |
| 8,175,698 B2 | 5/2012 | Palti et al. |
| 8,229,555 B2 | 7/2012 | Palti |
| 8,244,345 B2 | 8/2012 | Palti |
| 8,406,870 B2 | 3/2013 | Palti |
| 8,447,395 B2 | 5/2013 | Palti et al. |
| 8,447,396 B2 | 5/2013 | Palti et al. |
| 8,465,533 B2 | 6/2013 | Palti |
| 8,706,261 B2 | 4/2014 | Palti |
| 8,715,203 B2 | 5/2014 | Palti |
| 10,188,851 B2 | 1/2019 | Wenger et al. |
| 10,441,776 B2 | 10/2019 | Kirson et al. |
| 10,779,875 B2 | 9/2020 | Palti et al. |
| 10,821,283 B2 | 11/2020 | Giladi et al. |
| 11,160,977 B2 * | 11/2021 | Naveh ................ A61N 1/0476 |
| 11,369,790 B2 * | 6/2022 | Bomzon ............ A61N 1/36002 |
| 2006/0167499 A1 | 7/2006 | Palti |
| 2007/0225766 A1 | 9/2007 | Palti |
| 2007/0239213 A1 | 10/2007 | Palti |
| 2009/0076366 A1 | 3/2009 | Palti |
| 2009/0254019 A1 | 10/2009 | Gehl et al. |
| 2011/0137229 A1 * | 6/2011 | Palti .................... A61N 1/0428 604/20 |
| 2012/0283726 A1 | 11/2012 | Palti |
| 2013/0053905 A1 * | 2/2013 | Wagner ............. A61N 1/36021 607/45 |
| 2014/0330268 A1 | 11/2014 | Palti et al. |
| 2017/0120041 A1 * | 5/2017 | Wenger .................. A61B 5/24 |
| 2017/0215939 A1 | 8/2017 | Palti et al. |
| 2017/0281934 A1 | 10/2017 | Giladi et al. |
| 2018/0001075 A1 | 1/2018 | Kirson et al. |
| 2018/0001078 A1 * | 1/2018 | Kirson .................. A61N 1/044 |
| 2018/0008708 A1 | 1/2018 | Giladi et al. |
| 2018/0050200 A1 | 2/2018 | Wasserman et al. |
| 2018/0085575 A1 | 3/2018 | Travers et al. |
| 2018/0160933 A1 | 6/2018 | Urman et al. |
| 2018/0202991 A1 | 7/2018 | Giladi et al. |
| 2019/0117956 A1 | 4/2019 | Wenger et al. |
| 2019/0117963 A1 | 4/2019 | Travers et al. |
| 2019/0307781 A1 | 10/2019 | Krex et al. |
| 2019/0308016 A1 | 10/2019 | Wenger et al. |
| 2020/0001069 A1 | 1/2020 | Kirson et al. |
| 2020/0009376 A1 | 1/2020 | Chang et al. |
| 2020/0009377 A1 | 1/2020 | Chang et al. |
| 2020/0016067 A1 | 1/2020 | Gotlib et al. |
| 2020/0023179 A1 | 1/2020 | Bomzon et al. |
| 2020/0061360 A1 | 2/2020 | Hagemann et al. |
| 2020/0061361 A1 | 2/2020 | Hagemann et al. |
| 2020/0069937 A1 | 3/2020 | Naveh et al. |
| 2020/0078582 A1 | 3/2020 | Alon et al. |
| 2020/0108031 A1 | 4/2020 | Borst et al. |
| 2020/0121728 A1 | 4/2020 | Wardak et al. |
| 2020/0129761 A1 | 4/2020 | Bomzon et al. |
| 2020/0146586 A1 | 5/2020 | Naveh et al. |
| 2020/0155835 A1 | 5/2020 | Wasserman et al. |
| 2020/0171297 A1 | 6/2020 | Kirson et al. |
| 2020/0179512 A1 | 6/2020 | Giladi et al. |
| 2020/0219261 A1 | 7/2020 | Shamir et al. |
| 2020/0254242 A1 | 8/2020 | Chang et al. |
| 2020/0269037 A1 | 8/2020 | Hagemann et al. |
| 2020/0269041 A1 | 8/2020 | Zeevi et al. |
| 2020/0269042 A1 | 8/2020 | Giladi et al. |
| 2020/0269043 A1 | 8/2020 | Wasserman et al. |
| 2020/0306531 A1 | 10/2020 | Tran et al. |
| 2020/0330755 A1 | 10/2020 | Wasserman et al. |
| 2020/0368525 A1 | 11/2020 | Maag et al. |

* cited by examiner

DELIVERING TUMOR TREATING FIELDS (TTFIELDS) TO THE NECK

CROSS REFERENCE TO RELATED APPLICATIONS

This Application claims the benefit of U.S. Provisional Application 62/893,876, filed Aug. 30, 2019, which is incorporated herein by reference in its entirety.

BACKGROUND

TTFields are low intensity (e.g., 1-4 V/cm) alternating electric fields within the intermediate frequency range (e.g., 100-300 kHz), which may be used to treat tumors as described in U.S. Pat. No. 7,565,205, which is incorporated herein by reference in its entirety. TTFields therapy is an approved mono-treatment for recurrent glioblastoma (GBM), and an approved combination therapy with chemotherapy for newly diagnosed GBM patients. TTFields can also be used to treat tumors in other parts of a person's body (e.g. lungs, ovaries, pancreas). TTFields are induced non-invasively into the region of interest by transducer arrays (i.e., arrays of capacitively coupled electrode elements) placed directly on the patient's body (e.g., using the Novocure Optune™ system), and applying AC voltages between the transducer arrays.

In the context of GBM, the conventional approach for positioning the transducer arrays is to position the first pair of transducer arrays on the front and back of the head, and to position the second pair of transducer arrays on the right and left sides of the head. And in the context of treating mesothelioma, a conventional approach for positioning the transducer arrays is to position the first pair of transducer arrays on the front and back of the torso, and to position the second pair of transducer arrays on the right and left sides of the torso. An AC voltage generator applies an AC voltage (e.g., 200 kHz in the context of GBM or 150 kHz in the context of mesothelioma) between the first pair of transducer arrays for a first interval of time (e.g., one second), which generates an electric field with field lines that generally run in the front-back direction. Then, the AC voltage generator applies an AC voltage at the same frequency between the second pair of transducer arrays for a second interval of time (e.g., one second), which generates an electric field with field lines that generally run in the right-left direction. The system then repeats this two-step sequence for the duration of the treatment.

SUMMARY OF THE INVENTION

One aspect of the invention is directed to a first method of treating a tumor or preventing metastases in or near a person's neck. The first method comprises affixing a first set of electrode elements having a first centroid to the person's head with the first centroid positioned on the person's head; affixing a second set of electrode elements to the person's chest; and applying an alternating voltage between the first set of electrode elements and the second set of electrode elements. The applying is performed after affixing the first and second sets of electrode elements.

In some instances of the first method, the electrode elements of the first and second sets are capacitively coupled. In some instances of the first method, the alternating voltage that is applied between the first set of electrode elements and the second set of electrode elements has a frequency between 100 kHz and 300 kHz. In some instances of the first method, the first set of electrode elements comprises a plurality of electrode elements wired in parallel, and the second set of electrode elements comprises a plurality of electrode elements wired in parallel. In some instances of the first method, the first centroid is positioned on the vertex of the head. In some instances of the first method, the first centroid is positioned on an upper surface of the person's head. In some instances of the first method, the second set of electrode elements is positioned immediately below the base of the neck.

Another aspect of the invention is directed to a second method of planning the positioning of first and second sets of electrode elements on a subject's body. The second method comprises obtaining a 3D model of electrical conductivity or resistivity of an anatomic volume located in or near a person's neck within the subject's body at a given frequency; and identifying a location of target tissue within the anatomic volume. The second method also comprises analyzing electric fields associated with a plurality of layouts for the first and second sets of electrode elements based on the respective layouts, the 3D model of electrical conductivity or resistivity, and the identified location of the target tissue; and selecting one of the plurality of layouts based on a result of the analyzing. The first set of electrode elements has a first centroid. In each of the plurality of layouts, (a) the first set of electrode elements is positioned on the person's head with the first centroid positioned on the person's head, and (b) the second set of electrode elements is positioned on the person's chest.

In some instances of the second method, the first centroid is positioned on the vertex of the head. In some instances of the second method, the first centroid is positioned on an upper surface of the person's head. In some instances of the second method, the second set of electrode elements is positioned immediately below the base of the neck. In some instances of the second method, the given frequency is between 100 and 300 kHz. In some instances of the second method, the 3D model of electrical conductivity or resistivity is a 3D model of electrical conductivity.

Some instances of the second method further comprise the steps of affixing the first and second sets of electrode elements to the subject's body at positions that correspond to the selected layout; and applying electrical signals between the first and second sets of electrode elements subsequent to the affixing step, so as to impose an electric field in the target tissue.

Another aspect of the invention is directed to a third method of treating a tumor or preventing metastases in or near a person's neck. The third method comprises affixing a first set of electrode elements to the back of the person's neck; affixing a second set of electrode elements to the person's chest; and applying an alternating voltage between the first set of electrode elements and the second set of electrode elements. The applying is performed after affixing the first and second sets of electrode elements.

In some instances of the third method, the electrode elements of the first and second sets are capacitively coupled. In some instances of the third method, the alternating voltage that is applied between the first set of electrode elements and the second set of electrode elements has a frequency between 100 kHz and 300 kHz. In some instances of the third method, the first set of electrode elements comprises a plurality of electrode elements wired in parallel, and the second set of electrode elements comprises a plurality of electrode elements wired in parallel. In some instances of the third method, the second set of electrode elements is positioned immediately below the base of the neck.

BRIEF DESCRIPTION OF THE DRAWINGS

Various embodiments are described in detail below with reference to the accompanying drawings, wherein like reference numerals represent like elements.

DESCRIPTION OF THE PREFERRED EMBODIMENTS

Figure 1A:
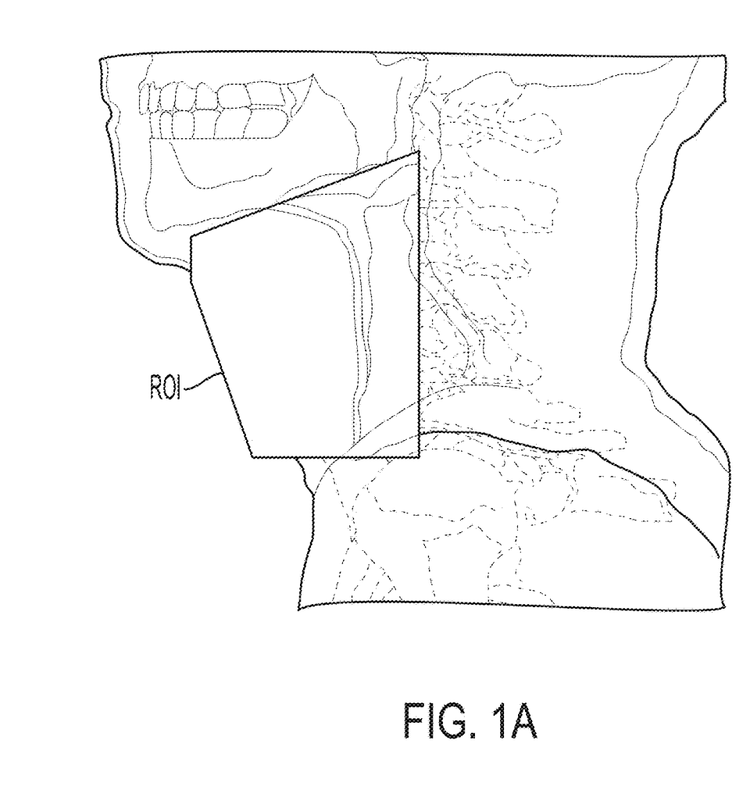
FIGS. 1A and 1B depict a region of interest where TTFields can be used to treat cancer using the transducer array layouts described herein.
Figure 1B:
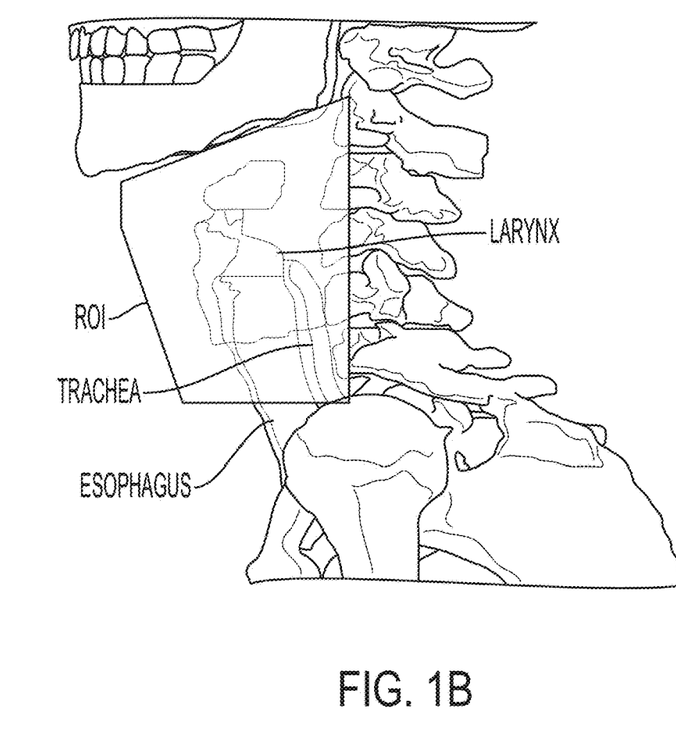

This application describes a number of transducer array layouts and may be used to treat cancers in the region of interest (ROI) depicted in FIGS. 1A and 1B. This ROI was taken about the larynx, and included all tissues except for the spinal bones, intervertebral discs and internal air.

In the context of treating brain tumors, positioning one pair of transducer arrays on the front and back of the head and another pair of transducer arrays on the left and right of the head is a practical approach. But in the context of treating tumors in the neck, positioning transducer arrays on all four sides of the neck would be uncomfortable and could limit the patient's movement. The transducer array layouts described in this application provide improved comfort and range of motion with respect to the conventional four-sided approach.

Pre-clinical experiments suggest that in order for TTFields to exert a therapeutic effect, field intensities should exceed a threshold of about 1 V/cm. But in the context of treating cancer in the ROI depicted in FIGS. 1A and 1B (e.g., upper neck cancers, such as head and neck squamous cell carcinomas (SCCs) and some cases of esophageal SCC and adenocarcinomas) many layouts for positioning the transducer arrays do not provide the desired level of field intensities.

Figure 2A:
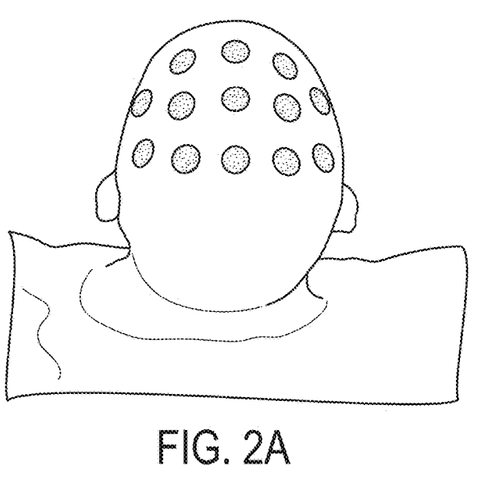
FIGS. 2A and 2B depict one example of a transducer array layout that provides adequately high field intensities in the region of interest.
Figure 2B:
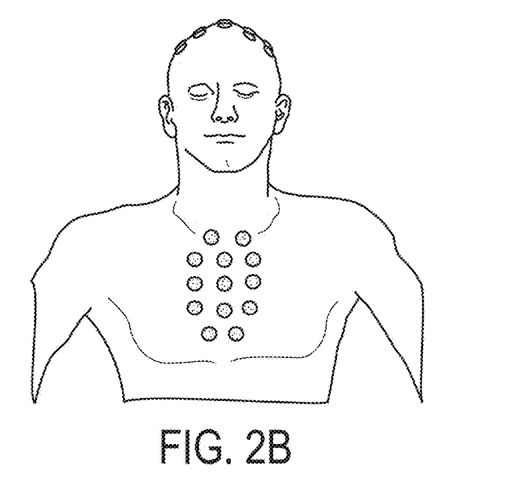
Figures 2C, 2D:
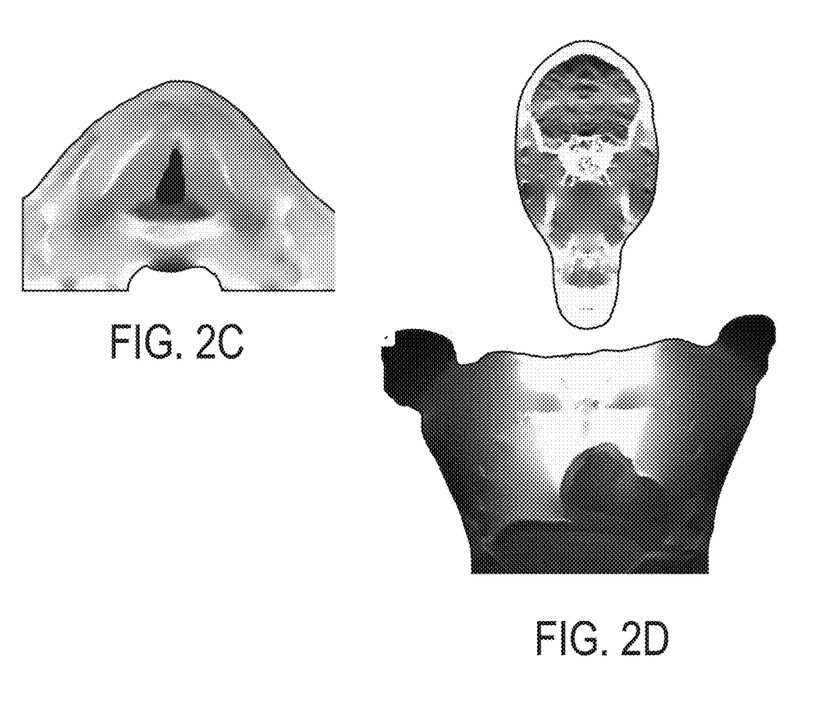
FIGS. 2C and 2D depict greyscale maps of the field intensities for the FIG. 2A/2B layout.
Figure 8:
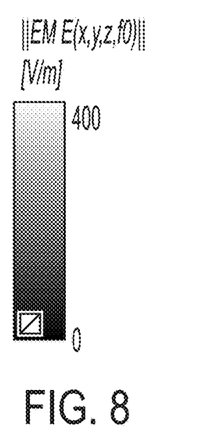
FIG. 8 depicts the scale for all grayscale maps in this application.

FIGS. 2A and 2B depict an example of a layout for one pair of transducer arrays that provides adequately high field intensities in the region of interest. In this layout, one transducer array that includes 13 round electrode elements (hereinafter referred to as discs) is positioned with its centroid on the vertex of the head and on an upper surface of the subject's head, and another transducer arrays that includes 13 discs is positioned on the upper chest, oriented vertically. Greyscale maps of the resulting field intensities for this layout are depicted in FIGS. 2C and 2D. (FIG. 8 depicts the scale for all the grayscale maps in this application.) For this layout, the mean intensity was 3.4 V/cm, the median field intensity was 3.41 V/cm, and 99.27% of the region of interest had an intensity above 1 V/cm.

Figure 3A:
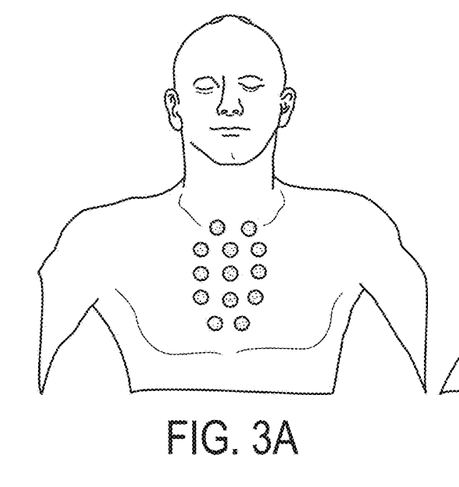
FIGS. 3A and 3B depict another example of a transducer array layout that provides adequately high field intensities in the region of interest.
Figure 3B:
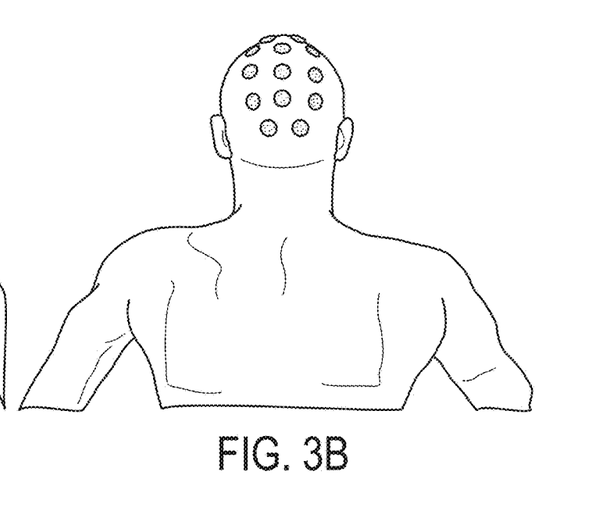
Figure 3C:
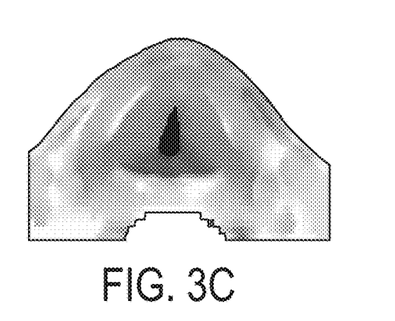
FIGS. 3C and 3D depict greyscale maps of the field intensities for the FIG. 3A/3B layout.
Figure 3D:
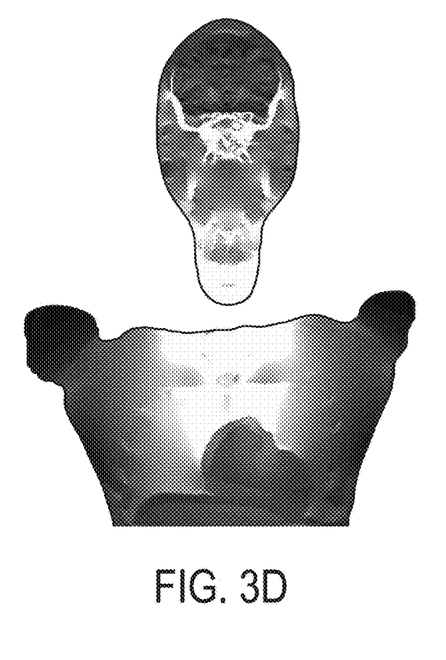

FIGS. 3A and 3B depict an example of another layout for one pair of transducer arrays that provides adequately high field intensities in the region of interest. In this layout, one transducer array that includes 13 round discs is positioned on the upper back of the subject's head, and another transducer arrays that includes 13 discs is positioned on the upper chest, oriented vertically. Greyscale maps of the resulting field intensities for this layout are depicted in FIGS. 3C and 3D. For this layout, the mean intensity was 3.22 V/cm, the median field intensity was 3.25 V/cm, and 99.07% of the region of interest had an intensity above 1 V/cm.

Figure 4A:
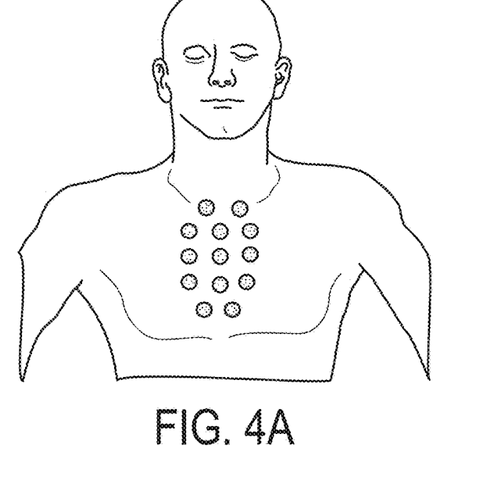
FIGS. 4A and 4B depict another example of a transducer array layout that provides adequately high field intensities in the region of interest.
Figure 4B:
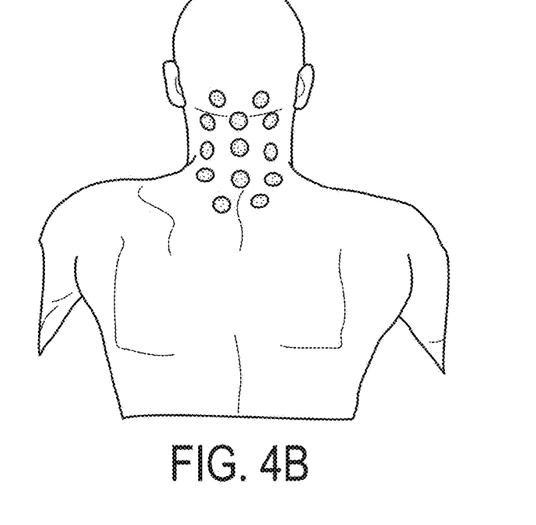
Figure 4C:
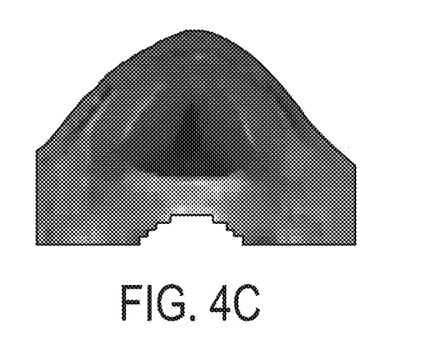
FIGS. 4C and 4D depict greyscale maps of the field intensities for the FIG. 4A/4B layout.
Figure 4D:
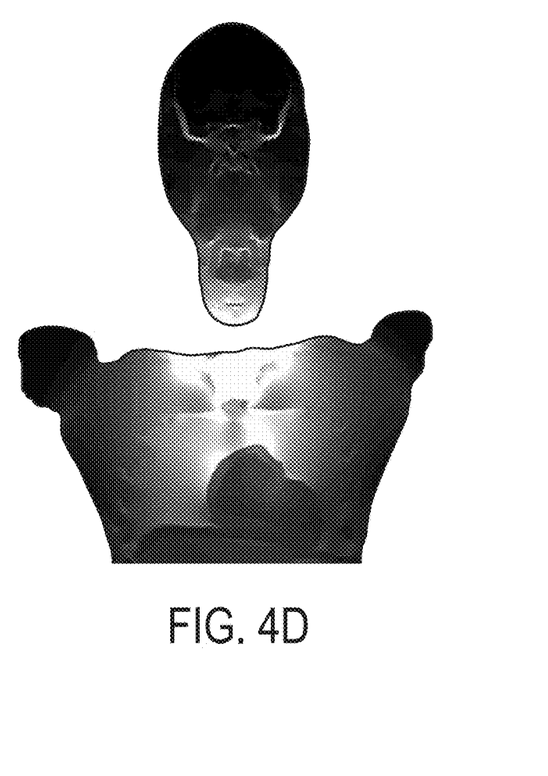

FIGS. 4A and 4B depict an example of another layout for one pair of transducer arrays that provides adequately high field intensities in the region of interest. In this layout, one transducer array that includes 13 round discs is positioned on the back of the subject's neck, and another transducer arrays that includes 13 discs is positioned on the upper chest, oriented vertically. Greyscale maps of the resulting field intensities for this layout are depicted in FIGS. 4C and 4D. For this layout, the mean intensity was 1.47 V/cm, the median field intensity was 1.39 V/cm, and 73.22% of the region of interest had an intensity above 1 V/cm. Notably, the results for this layout are not as good as for the layouts depicted in FIGS. 2 and 3.

Figure 5A:
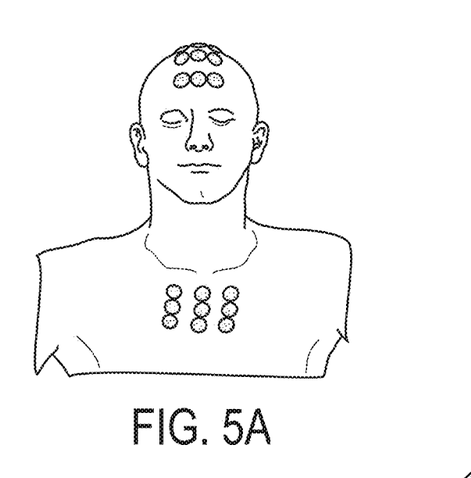
FIG. 5A depicts another example of a transducer array layout that provides adequately high field intensities in the region of interest.
Figure 5B:
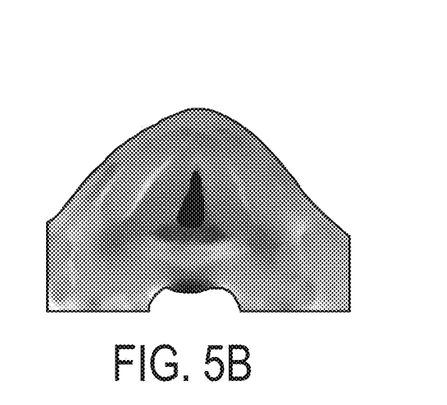
FIGS. 5B and 5C depict greyscale maps of the field intensities for the FIG. 5A layout.
Figure 5C:
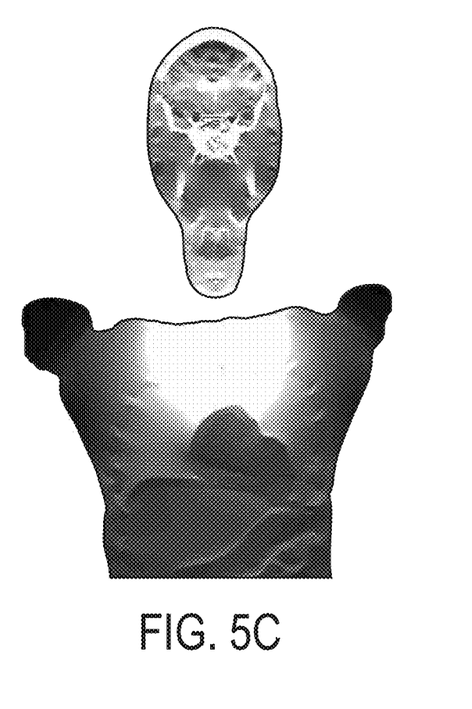

FIG. 5A depicts an example of another layout for one pair of transducer arrays that provides adequately high field intensities in the region of interest. In this layout, one transducer array that includes 9 round discs is positioned on the front top of the subject's head, and another transducer arrays that includes 9 discs is positioned on the upper chest, oriented horizontally. Greyscale maps of the resulting field intensities for this layout are depicted in FIGS. 5B and 5C. For this layout, the mean intensity was 2.55 V/cm, the median field intensity was 2.55 V/cm, and 98.79% of the region of interest had an intensity above 1 V/cm.

Figure 6A:
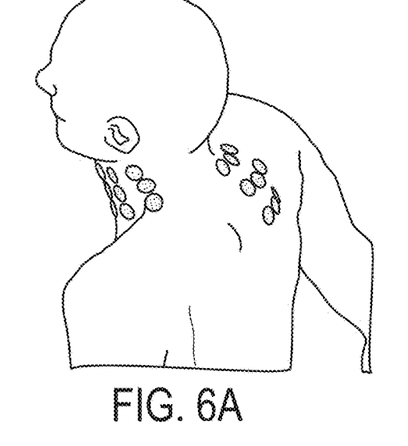
FIG. 6A depicts one example of an inferior transducer array layout.
Figure 6B:
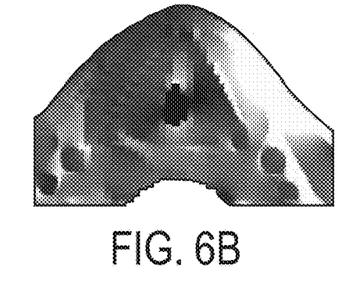
FIGS. 6B and 6C depict greyscale maps of the field intensities for the FIG. 6A layout.
Figure 6C:
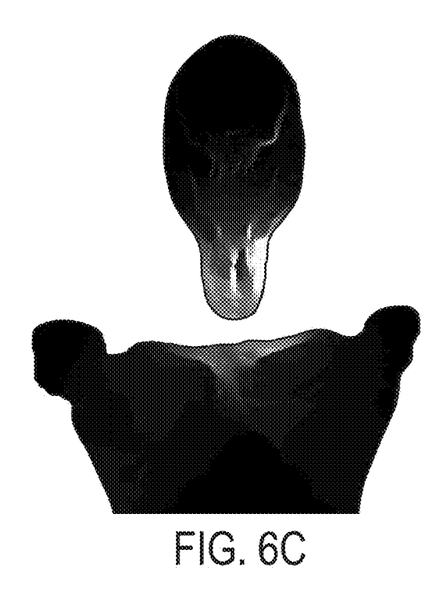

In contrast to the layouts described above, other layouts did not provide adequately high field intensities in the region of interest. For example, in the FIG. 6A layout, one transducer array that includes 9 round discs is positioned on the left side of the subject's neck, and another transducer arrays that includes 9 discs is positioned just to the right of the subject's spine at shoulder height. Greyscale maps of the resulting field intensities for this layout are depicted in FIGS. 6B and 6C. For this layout, the mean intensity was 1.83 V/cm, the median field intensity was 1.32 V/cm, and 64.83% of the region of interest had an intensity above 1 V/cm. Note that even though these numeric results do not seem that bad, these numeric results are misleading because most of the energy is dissipated on the skin, as seen clearly in FIGS. 6B and 6C.

Figure 7A:
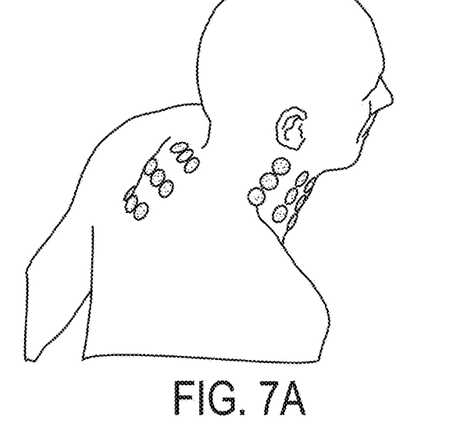
FIG. 7A depicts another example of an inferior transducer array layout.
Figure 7B:
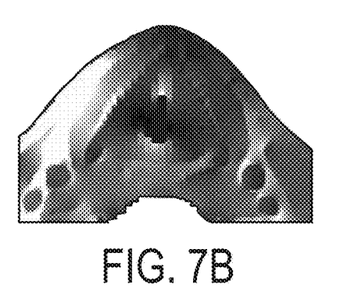
FIGS. 7B and 7C depict greyscale maps of the field intensities for the FIG. 7A layout.
Figure 7C:
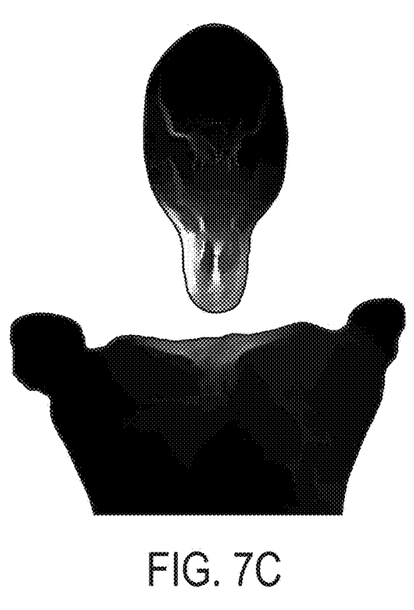

In the FIG. 7A layout, one transducer array that includes 9 round discs is positioned on the right side of the subject's neck, and another transducer arrays that includes 9 discs is positioned just to the left of the subject's spine at shoulder height. Greyscale maps of the resulting field intensities for this layout are depicted in FIGS. 7B and 7C. For this layout, the mean intensity was 1.67 V/cm, the median field intensity was 1.21 V/cm, and 60.10% of the region of interest had an intensity above 1 V/cm. Here again, even though these numeric results do not seem that bad, these numeric results are misleading because most of the energy is dissipated on the skin, as seen clearly in FIGS. 7B and 7C.

Note that all of the field intensities depicted and described herein were generated by running simulations at 150 kHz using a DUKE model by ZMT (Zurich). The simulated layouts used either 9 disc or 13 disc transducer arrays. The 9 disc simulations were normalized to 1 A current while the 13 disc simulations were normalized to 1.3 A current. The results show that placing one transducer array on t upper scalp and another on the upper chest deliver no less than 1.47 V/cm and up to 3.4 V/cm to the region of interest. This holds true when using either 9 disc arrays or 13 disc arrays. And as the upper array is moved lower, the field intensities drop. This was particularly notable in the FIG. 4 embodiment, where field intensity dropped to less than half of the FIG. 2 embodiment.

The same construction for the transducer arrays that is used in other anatomic locations may be used when the transducer arrays are positioned as described above. Examples of conventional transducer arrays are the transducer arrays used with the Novocure Optune® system. These transducer arrays have a flexible backing that is configured for affixation to person's body. Suitable materials for the flexible backing include cloth, foam, and flexible plastic (e.g., similar to corresponding materials used in bandages). A plurality of capacitively coupled electrode elements are positioned on the inner side of the flexible backing, and each of the capacitively coupled electrode elements has a conductive plate with a dielectric layer disposed thereon that faces inward. Optionally, temperature sensors (e.g., thermistors) may be positioned beneath each of the electrode elements in a manner that is similar to the conventional arrangement used in the Novocure Optune® system.

A set of conductors connects to the conductive plates of each of the plurality of capacitively coupled electrode elements. The conductors may be implemented using, for example, discrete wiring or using traces on a flex circuit. A layer of adhesive is configured to hold portions of the flexible backing that are not covered by any of the electrode elements against the person's body.

In the embodiments depicted in FIGS. 2-5, each transducer array is configured as an array of 9 or 13 individual electrode element discs, and the centroid of the array coincides with the center of the center disc. But in alternative embodiments, each transducer array may include a different number (e.g., between 4 and 24) of electrode elements. For example, a given transducer array may be configured as a 2×2 array of individual electrode element discs. In this situation, the centroid could be in a region that is located between all four discs. In other alternative embodiments, a given set of electrode elements may include only a single electrode element (which may be any suitable shape including but not limited to round and rectangular). In this situation, the centroid would coincide with the center of that single electrode element. Note also that in the embodiments described herein, the upper and lower transducer arrays each use the same number of discs. But in alternative embodiments, the number of discs on the upper and lower transducer arrays could be different (e.g., 9 discs on the upper array and 13 discs on the lower array).

Alternative constructions for the transducer arrays may also be used, including, for example, transducer arrays that use ceramic elements that are not disc-shaped, and transducer arrays that use non-ceramic dielectric materials positioned over a plurality of flat conductors. Examples of the latter include polymer films disposed over pads on a printed circuit board or over flat pieces of metal. Transducer arrays that use electrode elements that are not capacitively coupled may also be used. In this situation, each element of the transducer array would be implemented using a region of a conductive material that is configured for placement against a person's body, with no insulating dielectric layer disposed between the conductive elements and the body. Other alternative constructions for implementing the transducer arrays may also be used, as long as they are (a) capable of delivering TTFields to the person's body and (b) positioned in the locations specified herein. Optionally, a layer of hydrogel may be disposed between the transducer arrays and the person's body in any of the embodiments described herein.

For the layouts depicted above in connection with FIGS. 2-7, the mean intensity, the median field intensity, and the percentage of the ROI with an intensity above 1 V/cm were all obtained by simulating the electric fields when the electrode elements within each transducer array were positioned as depicted in FIGS. 2-7. Note, however, that the positions of the transducer arrays (and/or the elements within each of those arrays) may be varied from the exact locations depicted in those figures, as long as the movement is small enough so that the respective anatomic description above remains unchanged. For example, the electrode elements positioned on the head in FIG. 3B can move up, down, or to either side, as long as they remain positioned on the upper back of the subject's head. Similarly, the electrode elements positioned on the chest in FIG. 3A can move up, down, or to either side, as long as they remain on the upper chest.

Within this limited range of movement, the optimum position of each of the transducer arrays may be determined using simulations (e.g., finite element simulations) for each individual person to calculate the resulting electric field for each combination of positions for the transducer arrays, and selecting the combination that provides the best results (e.g., the highest percentage of the ROI with an intensity above 1 V/cm). An indication of the selected combination is then output to the care provider using, for example, a suitable display or printout. The care provider will then apply the transducer arrays to the person at the positions indicated by the output, hook the sets of electrode elements up to an AC signal generator 50, and commence TTFields treatment.

Figure 9:
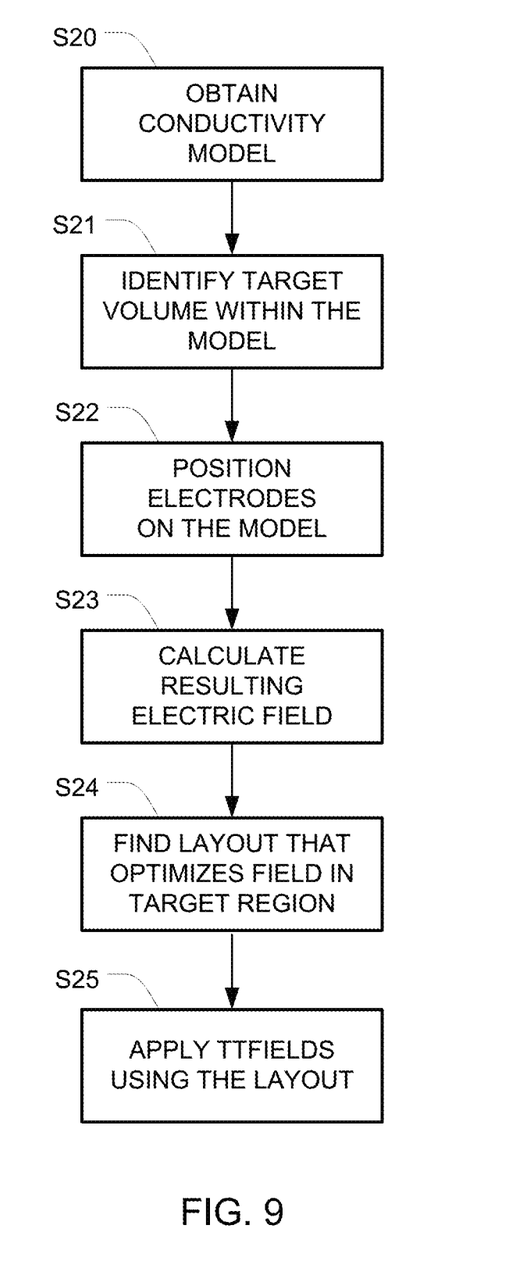
FIG. 9 depicts one example of how to use simulations to determine the optimal position of each of the transducer arrays.

FIG. 9 depicts one example of using simulations to determine the optimal position of each of the transducer arrays. First, in step S20, a 3D model of AC electrical conductivity (at the frequency that will be used for the TTFields treatment) of the relevant anatomic volume is obtained using any of a variety of approaches that will be apparent to persons skilled in the relevant arts. This model specifies the conductivity of each voxel.

Optimization of array layouts means finding the array layout that optimizes the electric field within the ROI. This optimization may be implemented by performing the following four steps: (S21) identifying the volume targeted for treatment (target volume) within the model; (S22) automatically placing transducer arrays and setting boundary conditions on the model; (S23) calculating the electric field that develops within the model once arrays have been placed on the model and boundary conditions applied; and (S24) running an optimization algorithm to find the layout that yields optimal electric field distributions within the target volume. One detailed example for implementing these four steps is provided below, but alternative approaches that will be apparent to persons skilled in the relevant arts can be substituted for the steps described below.

Step S21 involves locating the target volume within the model (i.e., defining a region of interest). A first step in finding a layout that yields optimal electric field distributions within the patient's body is to correctly identify the location and target volume, in which the electric field should be optimized.

In some embodiments, the target volume will be either the Gross Tumor Volume (GTV) or the Clinical Target Volume (CTV). The GTV is the gross demonstrable extent and location of the tumor, whereas the CTV includes the demonstrated tumors if present and any other tissue with presumed tumor. In many cases the CTV is found by defining a volume that encompasses the GTV and adding a margin with a predefined width around the GTV.

In order to identify the GTV or the CTV, it may be necessary to identify the volume of the tumor within MM images. This can be performed either manually by the user, automatically, or using a semi-automatic approach in which user-assisted algorithms are used. When performing this task manually, the Mill data could be presented to a user, and the user could be asked to outline the volume of the CTV on the data. The user could be asked to outline the CTV on a 3D volumetric representation of the Mills, or the user could be given the option of viewing individual 2D slices of the data, and marking the CTV boundary on each slice. Once the boundaries have been marked on each slice, the CTV within the anatomic volume (and hence within the model) can be found. In this case, the volume marked by the user would correspond to the GTV. In some embodiments, the CTV could then be found by adding margins of a predefined width to the GTV. Similarly, in other embodiments, the user might be asked to mark the CTV using a similar procedure.

An alternative to the manual approach is to use automatic segmentation algorithms to find the CTV. These algorithms perform automatic segmentation algorithms to identify the CTV using the structural Mill data.

Optionally, semi-automatic segmentation approaches of the Mill data may be implemented. In an example of these approaches, a user iteratively provides input into the algorithm (e.g., the location of the tumor on the images, roughly marking the boundaries of the tumor, demarcating a region of interest in which the tumor is located), which is then used by a segmentation algorithm. The user may then be given the option to refine the segmentation to gain a better estimation of the CTV location and volume within the body.

Whether using automatic or semi-automatic approaches, the identified tumor volume would correspond with the GTV, and the CTV could then be found automatically by expanding the GTV volume by a pre-defined amount (e.g., defining the CTV as a volume that encompasses a 20 mm wide margin around the tumor).

Note that in some cases, it might be sufficient for the user to define a region of interest in which they want to optimize the electric field. This region of interest might be for instance a box volume, a spherical volume, or volume of arbitrary shape in the anatomic volume that encompasses the tumor. When this approach is used, complex algorithms for accurately identifying the tumor may not be needed.

Step S22 involves automatically calculating the position and orientation of the arrays on the model for a given iteration. Each transducer array used for the delivery of TTFields comprises a set of ceramic disc electrodes, which are coupled to the patient's body through a layer of medical gel. When placing arrays on real patients, the discs naturally align parallel to the skin, and good electrical contact between the arrays and the skin occurs because the medical gel deforms to match the body's contours. However, virtual models are made of rigidly defined geometries. Therefore, placing the arrays on the model requires an accurate method for finding the orientation and contour of the model surface at the positions where the arrays are to be placed, as well as finding the thickness/geometry of the gel that is necessary to ensure good contact of the model arrays with the patient model. In order to enable fully automated optimization of field distributions these calculations have to be performed automatically.

A variety of algorithms to perform this task may be used, and one such algorithm is described in U.S. Pat. No. 10,188,851, which is incorporated herein by reference in its entirety.

Step S23 involves calculating the electric field distribution within the model for the given iteration. Once the model is constructed and the transducer arrays (i.e., the electrode arrays) that will be used to apply the fields are placed on the model, then a volume mesh, suitable for finite element (FE) method analysis, can be created. Next, boundary conditions can be applied to the model. Examples of boundary conditions that might be used include Dirichlet boundary (constant voltage) conditions on the transducer arrays, Neumann boundary conditions on the transducer arrays (constant current), or floating potential boundary condition that set the potential at that boundary so that the integral of the normal component of the current density is equal to a specified amplitude. The model can then be solved with a suitable finite element solver (e.g., a low frequency quasistatic electromagnetic solver) or alternatively with finite difference (FD) algorithms. The meshing, imposing of boundary conditions and solving of the model can be performed with existing software packages such as Sim4Life, Comsol Multiphysics, Ansys, or Matlab. Alternatively, custom computer code that realizes the FE (or FD) algorithms could be written. This code could utilize existing open-source software resources such as C-Gal (for creating meshes), or FREEFEM++ (software written in C++ for rapid testing and finite element simulations). The final solution of the model will be a dataset that describes the electric field distribution or related quantities such as electric potential within the computational phantom for the given iteration.

Step S24 is the optimization step. An optimization algorithm is used to find the array layout that optimizes the electric field delivery to the diseased regions of the patient's body (e.g., a tumor). The optimization algorithm will utilize the method for automatic array placement and the method for solving the electric field within the model in a well-defined sequence in order to find the optimal array layout. The optimal layout will be the layout that maximizes or minimizes some target function of the electric field in the diseased regions of the body. This target function may be for instance the maximum intensity within the diseased region or the average intensity within the diseased region. The optimal layout is selected for subsequent use.

There are a number of approaches that could be used to find the optimal array layouts for patients, two of which are described below. One optimization approach is an exhaustive search. In this approach the optimizer will include a bank with a finite number of array layouts that should be tested. The optimizer performs simulations of all array layouts in the bank (e.g., by repeating steps S22 and S23 for each layout), and picks the array layouts that yield the optimal field intensities in the tumor (the optimal layout is the layout in the bank that yields the highest (or lowest) value for the optimization target function, e.g., the electric field strength delivered to the tumor).

Another optimization approach is an iterative search. This approach covers the use of algorithms such as minimum-descent optimization methods and simplex search optimization. Using this approach, the algorithm iteratively tests different array layouts on the body and calculates the target function for electric field in the tumor for each layout. This approach therefore also involves repeating steps S22 and S23 for each layout. At each iteration, the algorithm automatically picks the configuration to test based on the results of the previous iteration. The algorithm is designed to converge so that it maximizes (or minimizes) the defined target function for the field in the tumor.

Note that alternative optimization schemes can be used to find an array layout that optimizes the electric field within diseased regions of the body. For example, algorithms that combine the various approaches mentioned above.

Once the layout that optimizes the electric field within the diseased regions of the patient's body has been determined (e.g., using any of the approaches explained herein), the electrodes can be affixed in the determined positions.

After affixing the transducer arrays as described above, we proceed to step S25, where an alternating voltage is applied between the transducer arrays (e.g., as described in U.S. Pat. No. 7,565,205, which is incorporated herein by reference) to treat the disease. In some embodiments, the frequency of the alternating voltage is between 100 kHz and 300 kHz. In some embodiments, the frequency of the alternating voltage is 150 kHz.

Advantageously, the layouts described herein can be used to deliver TTFields at therapeutically effective levels (i.e., greater than 1 V/cm) to the neck.

Note that while the embodiments described herein depict transducer arrays positioned on the surface of the subject's skin, the transducer arrays or a subset thereof may also be implanted beneath the surface of the subject's skin.

While the present invention has been disclosed with reference to certain embodiments, numerous modifications, alterations, and changes to the described embodiments are possible without departing from the sphere and scope of the present invention, as defined in the appended claims. Accordingly, it is intended that the present invention not be limited to the described embodiments, but that it has the full scope defined by the language of the following claims, and equivalents thereof.

What is claimed is:

1. A method of treating a tumor or preventing metastases in or near a person's neck, the method comprising:

affixing a first set of electrode elements having a first centroid to the person's head with the first centroid positioned on the person's head;

affixing a second set of electrode elements having a second centroid to a front of the person's upper chest with the second centroid positioned on the front of the person's upper chest; and applying an alternating voltage between the first set of electrode elements and the second set of electrode elements, wherein the applying is performed after affixing the first and second sets of electrode elements, and wherein the first and second sets of electrode elements are affixed at positions such that when the alternating voltage is applied between the first set of electrode elements and the second set of electrode elements, an electric field intensity greater than 1 V/cm is produced in a majority of a region of interest that includes all portions of the person's neck that are anterior to the person's spine.

2. The method of claim 1, wherein the electrode elements of the first and second sets are capacitively coupled.

3. The method of claim 1, wherein the alternating voltage that is applied between the first set of electrode elements and the second set of electrode elements has a frequency between 100 kHz and 300 kHz.

4. The method of claim 1, wherein the first set of electrode elements comprises a plurality of electrode elements wired in parallel, and wherein the second set of electrode elements comprises a plurality of electrode elements wired in parallel.

5. The method of claim 1, wherein the first centroid is positioned on the vertex of the head.

6. The method of claim 1, wherein the first centroid is positioned on an upper surface of the person's head.

7. The method of claim 1, wherein the second set of electrode elements is positioned immediately below the base of the neck.

8. A method of planning the positioning of first and second sets of electrode elements on a person's body, the method comprising the steps of:

obtaining a 3D model of electrical conductivity or resistivity of an anatomic volume within the person's body at a given frequency, wherein the anatomic volume is located in or near the person's neck;

identifying a location of target tissue within the anatomic volume;

analyzing electric fields associated with a plurality of layouts for the first and second sets of electrode elements based on the respective layouts, the 3D model of electrical conductivity or resistivity, and the identified location of the target tissue; and selecting one of the plurality of layouts based on a result of the analyzing, wherein the first set of electrode elements has a first centroid, and wherein in each of the plurality of layouts, (a) the first set of electrode elements is positioned on the person's head with the first centroid positioned on the person's head, and (b) the second set of electrode elements is positioned on the person's chest.

9. The method of claim 8, wherein the first centroid is positioned on the vertex of the head.

10. The method of claim 8, wherein the first centroid is positioned on an upper surface of the person's head.

11. The method of claim 8, wherein the second set of electrode elements is positioned immediately below the base of the neck.

12. The method of claim 8, wherein the given frequency is between 100 and 300 kHz.

13. The method of claim 8, further comprising the steps of:

affixing the first and second sets of electrode elements to the person's body at positions that correspond to the selected layout; and applying electrical signals between the first and second sets of electrode elements subsequent to the affixing step, so as to impose an electric field in the target tissue.

14. The method of claim 8, wherein the 3D model of electrical conductivity or resistivity is a 3D model of electrical conductivity.

15. A method of treating a tumor or preventing metastases in or near a person's neck, the method comprising:
affixing a first set of electrode elements to the back of the person's neck;
affixing a second set of electrode elements having a centroid to a front of the person's upper chest with the centroid positioned on the front of the person's upper chest; and
applying an alternating voltage between the first set of electrode elements and the second set of electrode elements,
wherein the applying is performed after affixing the first and second sets of electrode elements, and
wherein the first and second sets of electrode elements are affixed at positions such that when the alternating voltage is applied between the first set of electrode elements and the second set of electrode elements, an electric field intensity greater than 1 V/cm is produced in a majority of a region of interest that includes all portions of the person's neck that are anterior to the person's spine.

16. The method of claim 15, wherein the electrode elements of the first and second sets are capacitively coupled.

17. The method of claim 15, wherein the alternating voltage that is applied between the first set of electrode elements and the second set of electrode elements has a frequency between 100 kHz and 300 kHz.

18. The method of claim 15, wherein the first set of electrode elements comprises a plurality of electrode elements wired in parallel, and wherein the second set of electrode elements comprises a plurality of electrode elements wired in parallel.

19. The method of claim 15, wherein the second set of electrode elements is positioned immediately below the base of the neck.

20. The method of claim 1, wherein an electric field intensity greater than 1 V/cm is produced in at least 99% of the region of interest.

21. The method of claim 15, wherein an electric field intensity greater than 1 V/cm is produced in at least 73% of the region of interest.

\* \* \* \* \*